United States Patent [19]

Nakanishi et al.

[11] Patent Number: 4,820,641
[45] Date of Patent: Apr. 11, 1989

[54] MONOCLONAL ANTIBODY CAPABLE OF SPECIFICALLY DISTINGUISHING HUMAN HEPATO-CARCINOMA CELLS

[75] Inventors: Toshihiro Nakanishi, Ibaraki; Yoshiaki Fukuda, Takatsuki; Kenju Miura, Kyoto; Hiroshi Nakazato, Ibaraki, all of Japan

[73] Assignee: Suntory Limited, Osaka, Japan

[21] Appl. No.: 749,564

[22] Filed: Jun. 27, 1985

[30] Foreign Application Priority Data

Jun. 29, 1984 [JP] Japan .................... 59-134556

[51] Int. Cl.$^4$ .............. C12N 5/00; C12N 12/00; C07K 15/04
[52] U.S. Cl. ............... 435/240.27; 530/387; 424/1.1; 424/85.3; 435/68; 435/70; 435/172.2; 935/104; 935/107; 935/110
[58] Field of Search ........... 530/387, 388; 435/68, 435/70, 172.2, 240, 241, 948; 424/85, 1.1, 93; 935/100, 102–104, 107, 108, 110

[56] References Cited

U.S. PATENT DOCUMENTS 4,579,827  4/1986  Sakamoto .................... 436/536

OTHER PUBLICATIONS

Seto, M. et al., Cancer Research, 43: 4768–4773 (10–1983).
Seto, M. et al., Cancer Reserach, 46: 2056–2061 (4–1986).
Shouval, D. et al., Proc. Natl. Acad. Sci., U.S.A. 79(2): 650–654, (1982) cited in Biosis Abstract 82: 223133.
Sasanami, T., Sapporo Igaku Zasshi, 53(3): 223–241, (1984), cited in Chemical Abstract CA101(7): 53030v.
Miller et al.; Blood, vol. 58, No. 1 (Jul.) 1981; pp. 78–86; In Vivo Effects of Murine Hybridoma Monoclonal Antibody . . . Leukemia.
Hepatology, vol. 2, No. 5, 1982, p. 677; Antibodies to a Human Hepatoma Cell Line . . . Patterns.
Ritz et al.; Blood, vol. 58, No. 1 (Jul.) 1981; pp. 141–152; Serotherapy of Acute Lymphoblastic Leukemia with Monoclonal Antibody.

*Primary Examiner*—Margaret Moskowitz
*Attorney, Agent, or Firm*—Cushman, Darby & Cushman

[57] ABSTRACT

The specification discloses a monoclonal antibody capable of distinguishing human hepato-carcinoma cells, a hybridoma producing said monoclonal antibody and a process for preparing the monoclonal antibody using said hybridoma. The monoclonal antibody of the invention specifically attackes hepato-carcinoma cells in vivo.

7 Claims, 5 Drawing Sheets

MONOCLONAL ANTIBODY CAPABLE OF SPECIFICALLY DISTINGUISHING HUMAN HEPATO-CARCINOMA CELLS

BACKGROUND OF THE INVENTION

1. Field of the Invention

This invention relates to a monoclonal antibody (hereinafter at times referred to as a MoAb) capable of distinguishing human hepato-carcinoma cells, a hybridoma producing said monoclonal antibody and a process for preparing the monoclonal antibody by using said hybridoma. It also relates to the application of said monoclonal antibody. In particular, this invention relates to a monoclonal antibody which is capable of specifically distinguishing human hepato-carcinoma cells from normal cells and of damaging only hepato-carcinoma cells in vivo.

2. Prior Art

It was reported by Köehler and Milstein in 1975 that a hybridoma was prepared between P3X63-Ag8 (HGPRT-deficient strain), which is a mutant strain of mouse myeloma P3K, and a cell strain which produces anti-sheep red blood cell antibody, and that the hybridoma has self-growing ability and anti-sheep red blood cell antibody producing ability, as well. The concept of a homogeneous antibody which is capable of distinguishing only a single antigenic determinant, that is, the concept of the monoclonal antibody introduced in this research has received considerable attention in the fields of immunology, iatrology, pharmacology and biology. In 1977, H. Koprowski et al, at the Wistar Institute, prepared hybridomas which produce MoAb against viruses or malignant tumors. They showed the availability and effectiveness of the MoAb as an agent and suggested its possibility as a pharmaceutical agent. Since said antibody might specifically distinguish tumor specific antigens, their report with particular respect to the preparation of an anti-malignant tumor antibody has received considerable attention in the clinical field of the treatment of tumors where accompanying normal cell damage had previously been a problem. That is to say, an antibody capable of specifically distinguishing tumor specific antigens can specifically distinguish tumor cells without reacting with normal cells, even if both of the cells have been generated from the same individual. It has been expected that a treatment aiming at tumor cells as the sole targets may be realized if the antibody is cytotoxic in itself or otherwise combined with an anti-tumor agent.

For the purpose of realizing this expectation, attempts have been carried out to prepare MoAbs against various tumor cells [Proc. Natl. Acad. Sci. 75, 3405 (1978); Proc. Natl. Acad. Sci. 76, 1438 (1079); Proc. Natl. Acad. Sci. 77, 6841 (1980); Br. J. Cancer 43, 696 (1981)]. However, it has been found that the MoAbs thus obtained did not always distinguish only tumor specific antigens because they showed cross reactivity with normal cells, and further, that even if some of the MoAbs were found to be tumor specific, they showed that effect only on some limited leukemia cells while showing no therapeutic effect on solid tumors, such as hepatoma and the like, when applied to the treatment of tumors in vivo [Cancer Res., 40, 3147 (1980); Blood, 58, 141 (1981)].

Accordingly, the necessary prerequisites for an antibody applicable to the treatment of tumors is, first of all, that the antibody be specific to tumor cells and have no reactivity with normal cells, and secondly, that it be actually cytotoxic to tumor cells in vivo. However, no MoAb has been reported which satisfies both of these requirements and is effective as an antitumor agent. Furthermore, the MoAb prepared by this invention, which is useful for the treatment of hepato-carcinoma cells, has not been reported at all.

Most of the current treatments of hepato-carcinoma rely on excision, but such treatment by excision has a limit. Although it is said that up to 70–80% of liver volume can be excised, in the case of cirrhosis, there are sometimes cases where the regeneration of liver after excision cannot be expected, and in such cases, cirrhosis will be promoted after excision. Also, in the therapy of hepato-carcinoma with a drug such as a chemotherapeutic agent or the like, various attempts have been made including modification of the occasion, interval, route and site of the administration, but no reliable method or case has been reported showing a satisfactory therapeutic effect. Therefore, it is earnestly desired to develop a MoAb which is capable of specifically distinguishing hepato-carcinoma cells and specifically attacking them.

SUMMARY OF THE INVENTION

The object of this invention is to provide a MoAb which is capable of specifically distinguishing and attacking hepato-carcinoma cells in vitro and in vivo, a process for preparing said MoAb and an application of said MoAb as a diagnostic and/or therapeutic agent.

In particular, the object of this invention is to provide a MoAb which is specifically cytotoxic to human hepato-carcinoma cells and shows noticeable antitumor activity in vivo.

DETAILED DESCRIPTION OF THE INVENTION

Figure 1:
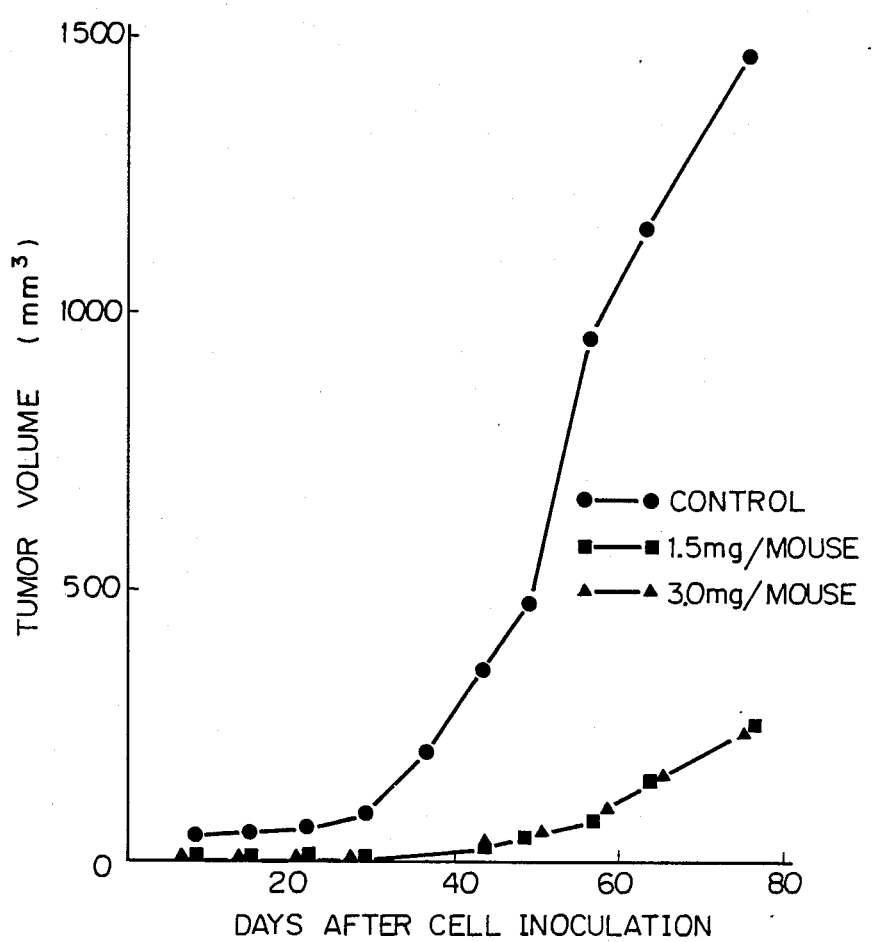
FIG. 1 is a graph which shows the antitumor effect of the monoclonal antibody according to this invention on a HC C-4 solid tumor model.

The antibody of this invention is a monoclonal antibody which is capable of specifically distinguishing human hepato-carcinoma cells.

The antibody of this invention is prepared by culturing the hybridoma according to this invention which is obtained by cell fusion between antibody-producing cells taken from a mammal immunized with human hepato-carcinoma cells and appropriate tumor cells derived from an animal, and subsequently cloning the fused cells which produce the desired antibody.

In order to obtain the hybridoma according to this invention, a mammal is first immunized with human hepato-carcinoma cells. A commonly used animal such as a mouse, a rat, a rabbit, a guinea pig and the like can be used as the mammal. For instance, a mouse is immunized by intraperitoneally or subcutaneously inoculating human hepato-carcinoma cells as the antigen. Inoculation is carried out in the range of $10^6$–$10^7$ cells/mouse at each inoculation and repeated several times, with an interval of 1 or 2 weeks therebetween. 1–5 days after the last inoculation, the spleen is removed and used to provide the antibody-producing cells. Next, a tumor cell strain, such as myeloma, which has a suitable selection marker, such as hypoxanthine-guanine-phosphoribosyl-transferase deficiency (HGPRT$^-$) or thymidine kinase deficiency (TK$^-$), is provided as a counterpart parent, which is allowed to fuse with the antibody-producing cells to obtain the hybridoma. Thus, the hybridoma is prepared.

The culture medium used in the preparation of the hybridoma may be selected from conventional culture medium, such as Eagle's MEM, Dulbecco's modified MEM, RPMI1640 or the like, which are supplemented with 10% CS (calf serum), 5% FCS (fetal calf serum)+5% CS or 10% FCS. Either of the aforementioned media is sufficient for the usual maintenance of the parent cell, while 10% FCS is preferred for the preparation of the hybridoma.

First of all, parent tumor cells, such as myeloma cells or the like, and spleen cells are provided in the proportion of 1:5. As a fusing agent, there may be mentioned HVJ (Hemagglutinating virus of Japan, which is also named Sendai virus), polyethylene glycol (PEG) or the like. In particular, PEG 1,000, prepared in a concentration of 30–50%, is preferred. The method of HAT selection of the fused strain is well known and is, for example, described in Japanese patent application No. 7744/1983 by the present inventor. In the screening of the resulting hybridoma, clones of the hybridoma secreting the desired immunoglobulin are picked up by a well-known method, such as the indirect rosette method (also named, the SPA-bind-SRBC method; SPA: *Staphylococcus aureus* protein A, SRBC: Sheep Red Blood Cell; MENEKI JIKKEN SOSAHO VII, p. 2375, 1979, edited by the Japanese Society for Immunology), ELISA (Enzyme linked immunosorbent assay) method (Dynatech method) or the like. Cells of each clone are allowed to gradually increase, and sub-cloning is carried out when the population of clones reaches about $10^5$ cells/ml. In order to examine the homogeneity of the hybridoma, a feeder layer of normal spleen cells is provided over a 96 well microtiter plate at a concentration of about $10^5$ cells/well, over which the hybridoma is plated so that the number does not exceed 1 cell/well (0.1 cells as the mean probability per well), and screening is again carried out for those clones which have been grown after about 1 week of cultivation. By repetition of this sub-cloning, the homogeneous hybridoma according to this invention is obtained.

Moreover, the tumor cells which may be employed as a parent in cell fusion are not restricted to mouse myeloma cells, but a human melanoma cell line may also be used for preparing a hybridoma, as disclosed in Japanese patent application No. 7744/83 by the present inventor.

Next, in order to prepare the monoclonal antibody of this invention which is specific to hepato-carcinoma, the hybridoma obtained above is cultured in a culture vessel (in vitro) or in an animal body (in vivo). In the cultivation in vitro, the medium may be a conventional medium with the addition of CS or FCS, as stated above. After cultivation for 3–5 days in this medium, MoAb is obtained from the supernatant of the culture. In the in vivo cultivation, the hybridoma is intraperitoneally inoculated to a mammal, and ascites is collected after 7–14 days, from which MoAb is obtained. The in vivo cultivation is preferred, because it can efficiently produce a much larger amount of antibody than the in vitro cultivation.

The MoAb obtained from the culture supernatant or the ascites can be purified by a combination of well-known methods, such as ammonium sulfate fractionation, use of a protein A Cepharose column and the like, e.g., in the same manner as will be described in Example 2.

Non-limiting examples are now described below, these Examples being carried out under the following conditions unless otherwise specified.

Incubation condition: 5% $CO_2$; 95% air; humidity, ca. 100%; temperature, 37° C.

Medium: RPMI1640+10% FCS (CSL Australia)

Animals:
BALB/c strain mouse (female, 4 weeks old) or
BALB/cA-nu/JCR strain nude mouse (female, 6 weeks old)
(both of them were purchased from Clea Japan Inc.)

Cells:
human hepatoma cells HC C-4
mouse myeloma P3X63-Ag8.653
(both of them are commonly used in the laboratories of universities or institutes and are easily obtainable)

EXAMPLE 1

Preparation of the Hybridoma

Cultured human hepatoma cells (HC C-4) were inoculated intraperitoneally to BALB/c strain mice at a concentration of $10^7$ cells/mouse at intervals of 1 week over a period of 4 weeks. 3 days after the last inoculation, the spleen was removed and a spleen cell suspension was prepared by pressing the spleen on a stainless mesh, thereby allowing the cells to be filtered in a medium. Culture of myeloma P3X63-Ag8.653 derived from BALB/c strain mouse at a concentration of $10^7$ were provided as parent cells for fusion.

Fusion was carried out in accordance with a well-known method [Nature, 256, 495 (1975)] as follows:

The above-obtained mouse spleen cells ($5 \times 10^7$) and myeloma cells ($1 \times 10^7$) were mixed in a centrifuge tube. After centrifugation, supernatant fluid was discarded, and about 0.5 ml of 40% polyethylene glycol (PEG 1,000, manufactured by Wako Pure Chemical Industries, Ltd.) in RPMI1640 was added to the packed cells. After the mixture was left standing for 3 minutes, it was centrifuged at 500 rpm for 3 minutes. Then, about 5 ml of the medium was added slowly, and the mixture was again centrifuged. The supernatant was discarded. Then all cells were slowly transferred into T-75 (Falcon No. 3024), to which the medium was added to bring the total volume up to about 40 ml, and the cells were incubated overnight. All of the incubated mixture, including the cells, was charged into a centrifuge tube and centrifuged. The supernatant was discarded. Then, 40 ml of a HAT medium (RPMI1640 medium supplemented with 10% FCS; $10^{-4}$ mole of hypoxanthine, $4 \times 10^{-7}$ mole of aminopterin and $1.6 \times 10^{-5}$ mole of thymidine were added to the final concentration) was added, and the cells were sufficiently mixed to provide a suspension that was then added to a 96 well microtiter plate (Coster No. 3596) at a concentration of about 100 μl/well. Upon cultivation in this state for 1 week, colonies were observed in about 30-50% of the wells. After a cultivation period of 1 week, a HT medium (having the same composition as a HAT medium except that aminopterin was absent) was added in an amount of one drop (about 25-30 μl) per well. After the colonies had grown to a certain extent (after 10-14 days), screening using the supernatant of the culture was carried out by the indirect rosette method to examine the colonies for secretion of the antibody against the desired human hepatoma (HC C-4). It was found that 4 colonies secreted the antibody against HC C-4. Using these 4 colonies, subscreening was carried out. That is to say, untreated BALB/c strain mouse spleen cells were spread over a 96 well microtiter plate at a concentration of $10^5$ cells/well as a feeder layer, over which the cells of the above-obtained colonies were spread such that the cell number was about 0.1 cell/well, and incubation was then carried out for 1 week. For the clones thus obtained, screening and subscreening was carried out, and 4 hybridomas producing monoclonal antibody against HC C-4 were finally obtained. One of these hybridomas was designated as HY-2014, and the monoclonal antibody obtained from the hybridoma was designated as HC-2014. The hybridoma HY-2014 was deposited at the Fermentation Research Institute (FERM), an authorized depository under the Budapest Treaty, on Nov. 10, 1987. The address of the depository is as follows: 1-3, Higashi 1-chome, Tsukuba-shi Ibaraki-Ken, 305 Japan. The purification of HC-2014 will now be described below.

EXAMPLE 2

Purification of the MoAb and Examination of its Specificity (a) Pristane (mineral oil) in an amount of 0.5 ml was intraperitoneally administered to a BALB/c strain mouse, and the HC-2014 producing hybridoma, $5 \times 10^6$ cells were intraperitonearly inoculated after 7 days so as to provide ascites. Two weeks after the administration, the ascites was collected, and the MoAb was purified by the following method.

First, 30 ml of the ascites thus obtained was centrifuged at 10,000 rpm for 15 minutes, and then ammonium sulfate was added to the supernatant to ensure a concentration of the salt of 33.3%. Salting out was carried out at 4° C. for 60 minutes. After centrifugation at 10,000 rpm for 15 minutes, the precipitate was dissolved in 5 ml of PBS (Phosphate Buffered Saline: 8.1 m mole $NaH_2PO_4$, 1.5 m mole $KH_2PO_4$, 2.7 m mole KCl, 137 m mole NaCl, pH 7.2) and dialyzed against 3 l of the same solution. After dialysis, the dialysate was introduced into a Protein A Cepharose column and eluted with a 0.1 mole acetic acid-PBS solution, and the eluate was neutralized with 0.1N NaOH.

The purified MoAb was stored at −80° C. in a freezer.

(b) The reactivities of MoAb prepared in (a) to HC C-4 and other various tumor cells were examined using the ELISA method and the indirect rosette method.

As antigens, the following cells were used:
HC H-4: human hepatoma cell used for producing the antibody
A 549: human lung carcinoma cell
KATO III: human gastric carcinoma cell
AZ 521: human gastric carcinoma cell
BM 314: human colon carcinoma cell.

Figure 4:
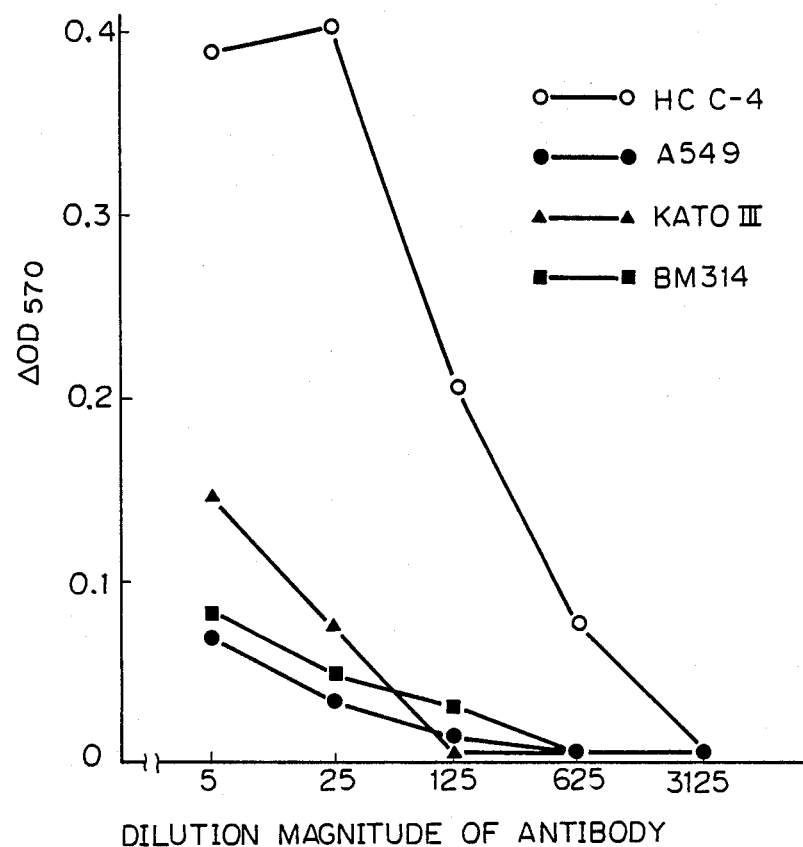
FIG. 4 is a graph which shows the test result of the specificity of the monoclonal antibody according to this invention by the ELISA method.

The reactivities were examined using the ELISA method by reacting these antigens with a series of 5-fold dilutions of MoAb HC-2014 over a range of 5- to 3125-fold dilution. A β-Galactosidase kit (manufactured by Zymed Laboratories; purchased from Maruzen) was used for the ELISA method. It will be seen in FIG. 4 that HC-2014 reacted only with the HC C-4 human hepatoma cell among the antigens used.

Also, using the indirect rosette method, HC-2014 formed a rosette only with HC C-4 human hepatoma cells as the antigen but reacted with other tumor cells, as shown in Table 1.

TABLE 1

| Results using the indirect rosette method | | |
|---|---|---|
| Cell Type | Cell Line | Rosette Formation |
| Lung carcinoma | A 549 | − |
| Colon carcinoma | BM 314 | − |
| Gastric carcinoma | KATO III | − |
| Gastric carcinoma | AZ 521 | − |
| Hepato-carcinoma | HC C-4 | + |

EXAMPLE 3

Examination of the Class and Sub-class of MoAb Using the Ouchterlony Method

Figure 5:
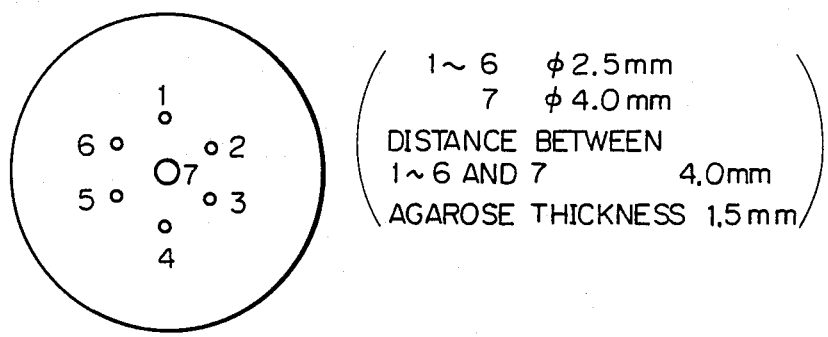
FIGS. 5 and 6 are illustrations of the Ouchterlony method for identifying the class and sub-class, respectively, of the monoclonal antibody in Example 2.

Class and sub-class of immunoglobulin were identified for the MoAb prepared in Example 2 using the Ouchterlony method. 1.5% agarose solution (containing 0.01% $NaN_3$) was added to petri dishes (internal diameter: 52 mm) in an amount of 5 ml each and allowed to stand for about 30 minutes until solidified. Then, wells were punched on the solidified agarose, as shown in FIG. 5. To respective well Nos. 1-6 were added 5 μl of the corresponding anti-immunoglobulin antibodies, and to central well No. 7 was added 1.5 μl of the monoclonal antibody purified in Example 2. The dishes were allowed to stand for 24 hours, and the class of the monoclonal antibody was determined depending on the inhibition line produced.

TABLE 2

| Antibody used for the determination of class | | |
|---|---|---|
| No. | Antibody | Source |
| 1 | Anti-human IgM | Rabbit (manufactured by Hoechst AG.) |
| 2 | anti-human IgG | Rabbit (manufactured by Hoechst AG.) |
| 3 | Anti-mouse IgG | Rabbit (manufactured by Cappel Lab.) |
| 4 | Anti-mouse IgM | Goat (manufactured by Hoechst AG.) |
| 5 | Anti-human Ig (G + A + M) | Goat (manufactured by Hoechst AG.) |
| 6 | Anti-human IgA | Rabbit (manufactured by Hoechst AG.) |

From the results it was found that the monoclonal antibody obtained was mouse IgG, because an inhibition line was formed between well Nos. 3 and 7.

Figure 6:
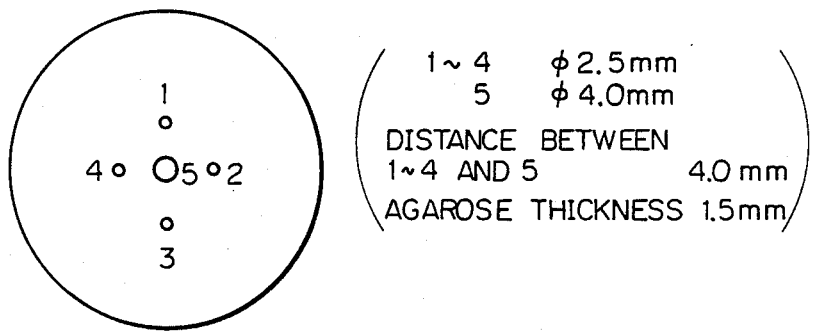

Next, in order to identify the sub-class of the IgG, the same experiment as above was carried out. That is, well Nos. 1-5 were punched on the agarose as shown in FIG. 6, and to these wells were added the corresponding antibodies of the respective sub-classes in the amounts of 5 μl each, while to central well No. 5 was added 15 μl of the monoclonal antibody (HC-2014) obtained above. The dishes were allowed to stand for 24 hours at room temperature.

TABLE 3

| No. | Antibody | Source |
|---|---|---|
| | Antibodies used for the determination of sub-class | |
| 1 | Anti-mouse IgG$_1$ | Rabbit (manufactured by Miles Lab.) |
| 2 | Anti-mouse IgG$_{2a}$ | Rabbit (manufactured by Miles Lab.) |
| 3 | Anti-mouse IgG$_{2b}$ | Rabbit (manufactured by Miles Lab.) |
| 4 | Anti-mouse IgG$_3$ | Rabbit (manufactured by Miles Lab.) |

From these results, it was found that the monoclonal antibody (HC-2014) obtained was IgG$_{2a}$, because an inhibition line was formed between well Nos. 2 and 5.

Further, the homogeneity of the antibody secreted by the hybridoma was confirmed using the SDS polyacrylamide gel electrophresis method.

EXAMPLE 4

In Vitro ADCC Activity of HC-2014

In an in vitro examination showing that the monoclonal antibody according to this invention is capable of attacking and killing human hepato-carcinoma cells in the presence of effector cells, the cytotoxicity of HC-2014 to the human hepatoma cells (HC C-4) was examined by the ADCC (antibody-dependent cell-mediated cytotoxicity) activity with a monoclonal antibody (YK 024) to human gastric carcinoma as a reference.

HC C-4 was spread over 96 well microtiter plates in the amount of $10^5$ cells/well and incubated overnight. To these plates was added the HC-2014 obtained in Example 2 or YK 024, in order to ensure that the concentrations were 0, 0.1, 0.5 and 2.5 μg/ml. The plates were allowed to stand in a CO$_2$ incubator for 30 minutes and then washed three times with PBS. Then, spleen cells derived from a BALB/c strain mouse were added as effector cells at a rate of $10^6$ cells/well and incubated overnight. Then, the plates were washed three times with PBS, and the survival of the HC C-4 in each of the wells was judged. Judgement was carried out by counting the viable cells after trypan blue staining.

The results are shown in Table 4, wherein cases having a survival rate of less than 10% are expressed as being positive (+) with respect to the ADCC activity.

TABLE 4

| Concentration of Antibody (μg/ml) | Monoclonal Antibody | | | |
|---|---|---|---|---|
| | HC-2014 Spleen Cells | | YK 024 Spleen Cells | |
| | − | + | − | + |
| 2.5 | − | + | − | − |
| 0.5 | − | + | − | − |
| 0.1 | − | + | − | − |
| 0 | − | − | − | − |

EXAMPLE 5

Antitumor Effect of HC-2014 on an Ascites Tumor Model

For the purpose of confirming that the monoclonal antibody according to this invention is cytotoxic to human hepato-carcinoma cells in vivo, as well as in vitro, a model test was carried out using nude mice.

Nude mice were divided into groups involving 6 mice in each group, and HC C-4 cells were intraperitoneally inoculated at a concentration of $2 \times 10^7$ cells. The day of the inoculation was set as day zero. On the 1st, 3rd and 5th days after inoculation, the MoAb HC-2014 prepared in Example 2 was intraperitoneally administered in an amount of 1.5 mg or 3.0 mg, and when the increased life span (ILS%), was calculated from the number of days of survival as compared to a non-administered control group, it was as high as 200% or more. Further, during and just after the administration of HC-2014, decrease of body weight and intoxication were not observed. Increased life span (ILS%) was calculated from the following equation:

$$ILS = \left( \frac{\text{Mean survival days of the administered group}}{\text{Mean survival days of the control group}} - 1 \right) \times 100\%$$

Figure 2:
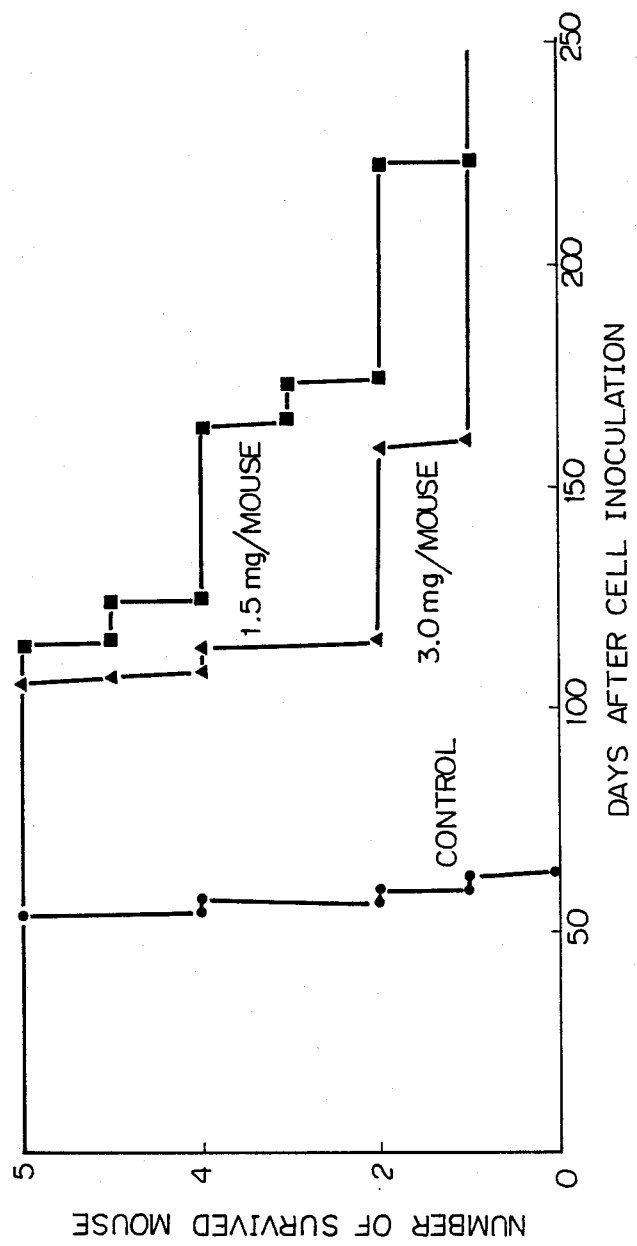
FIG. 2 is a graph which shows the antitumor effect of the monoclonal antibody according to this invention on a HC C-4 ascites tumor model.

The number of days of survival of respective groups are shown in FIG. 2.

Figure 3:
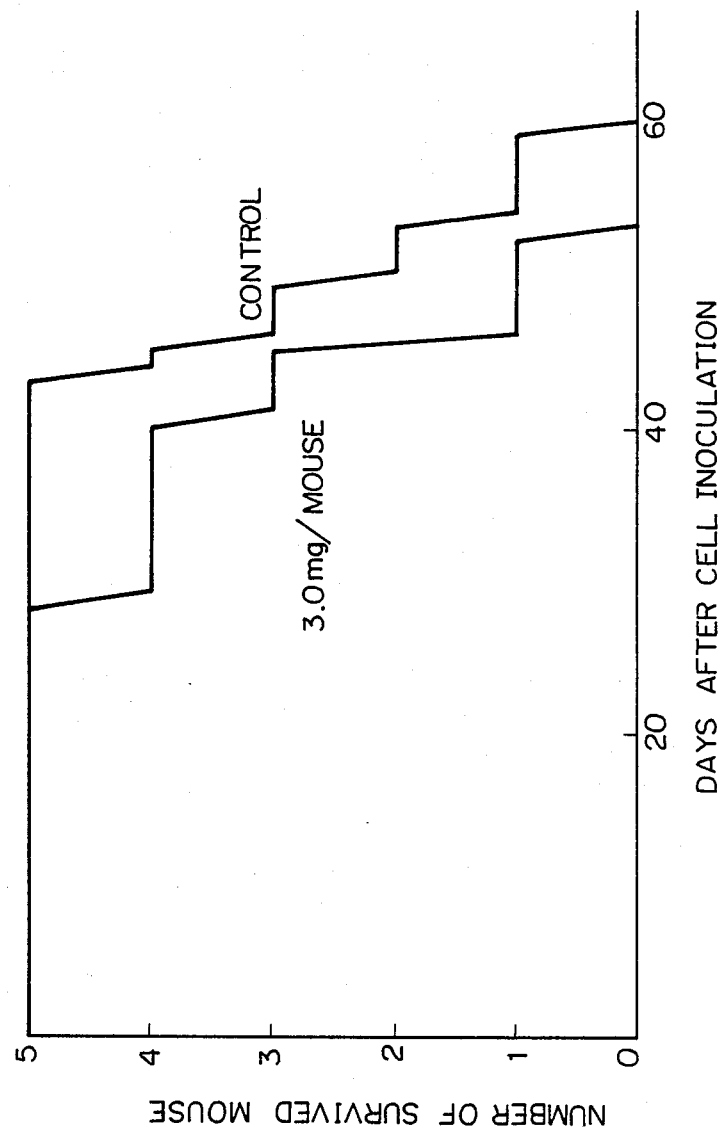
FIG. 3 is a graph which shows the result of a test replacing HC C-4 cells with BM314 cells.

On the other hand, when the experiment was repeated by replacing HC C-4 with BM 314 (cultured cell strain of human colon carcinoma), no difference was observed between the test group and the control group. The result is shown in FIG. 3.

EXAMPLE 6

Antitumor Effect of HC-2014 on a Solid Tumor Model

Nude mice were divided into groups including 6 mice in each group, and HC C-4 cells were subcutaneously inoculated at a portion under the back skin at a concentration of $1 \times 10^7$ cells (on day zero). In the same manner as in Example 5, HC-2014 was intraperitoneally administered on the 1st, 3rd and 5th days after inoculation in an amount of 1.5 mg or 3.0 mg. The volume of the tumor $$\left( \frac{\text{longer diameter} \times \text{shorter diameter}^2}{2} \right)$$

was measured and T/C % was calculated with the non-administered control group as a reference from the following equation:

$$T/C\% = \left( \frac{\text{Mean tumor volume of the administered group } (T)}{\text{Mean tumor volume of the control group } (C)} \right) \times 100\%$$

The result is shown in FIG. 1. As is apparent from the figure, T/C % was about 10% or less when one of the mice in the control group died (at 80 days). This indicates that the volume of the solid tumor on the back position was suppressed to 1/10 or less than that of the control group by the administration of the monoclonal antibody according to this invention.

The monoclonal antibody obtained by the present invention is capable of specifically binding only to human hepato-carcinoma cells, i.e., the immunogen, and shows ADCC activity in vitro and remarkable antitumor activity in vivo, and it can therefore be anticipated that the antibody of the invention has the possibility of being used as reagents and diagnostic agents in EIA, RIA or the like, as well as in therapy for hepatocarcinoma.

What is claimed is:

1. A monoclonal antibody belonging to sub-class IgG$_{2a}$ which is produced by hybridoma cell line HY-2014 and specifically binds to human hepato-carcinoma cells.

2. A monoclonal antibody according to claim 1, wherein said monoclonal antibody specifically binds to human hepato-carcinoma cells but does not bind to lung carcinoma cells, colon carcinoma cells or gastric carcinoma cells and is cytotoxic to human hepato-carcinoma cells in vivo and in vitro.

3. A monoclonal antibody according to claim 1, which is designated as HC-2014.

4. A monoclonal-antibody-producing hybridoma cell line characterized by the production of monoclonal antibody HC-2014 which specifically binds to human hepato-carcinoma cells.

5. A monoclonal-antibody-producing hybridoma cell line according to claim 4 which is designated as HY-2014.

6. A composition for the treatment of hepato-carcinoma, which comprises a monoclonal antibody according to claim 1 as an effective ingredient together with a pharmaceutically acceptable carrier.

7. A composition for the diagnosis of hepato-carcinoma, which comprises a monoclonal antibody according to claim 1 together with a carrier selected from water, physiological saline and phosphate buffered saline.

* * * * *